(12) United States Patent
Kaufman et al.

(10) Patent No.: US 11,357,725 B2
(45) Date of Patent: *Jun. 14, 2022

(54) DELIVERY OF AGENTS USING METASTABLE LIPOSOMES

(71) Applicant: Lipella Pharmaceuticals Inc., Pittsburgh, PA (US)

(72) Inventors: Jonathan H. Kaufman, Pittsburgh, PA (US); Michael B. Chancellor, Pittsburgh, PA (US)

(73) Assignee: LIPELLA PHARMACEUTICALS INC., Pittsburgh, PA (US)

( * ) Notice: Subject to any disclaimer, the term of this patent is extended or adjusted under 35 U.S.C. 154(b) by 18 days.

This patent is subject to a terminal disclaimer.

(21) Appl. No.: 16/866,140

(22) Filed: May 4, 2020

(65) Prior Publication Data
US 2020/0261364 A1    Aug. 20, 2020

Related U.S. Application Data

(63) Continuation of application No. 15/030,140, filed as application No. PCT/US2014/061769 on Oct. 22, 2014, now Pat. No. 10,639,278.
(Continued)

(51) Int. Cl.
*A61K 9/127* (2006.01)
*A61K 9/00* (2006.01)
(Continued)

(52) U.S. Cl.
CPC .......... *A61K 9/1272* (2013.01); *A61K 9/0034* (2013.01); *A61K 31/436* (2013.01); *A61K 49/0084* (2013.01)

(58) Field of Classification Search
CPC ..................... A61K 9/127; A61K 9/1272
See application file for complete search history.

(56) References Cited

U.S. PATENT DOCUMENTS

| 4,837,028 A   | 6/1989 | Allen |
| 4,999,208 A * | 3/1991 | Lengerich ............ A21C 11/163 426/243 |

(Continued)

FOREIGN PATENT DOCUMENTS

| JP | H1059840 | 3/1998 |
| WO | 2009139984 | 11/2009 |

OTHER PUBLICATIONS

E. D. Eanes and A. W. Hailer. "Liposome-Mediated Calcium Phosphate Formation in Metastable Solutions." Calcified Tissue International, vol. 37, 1985, pp. 390-394. (Year: 1985).*
(Continued)

*Primary Examiner* — Isaac Shomer
(74) *Attorney, Agent, or Firm* — Pabst Patent Group LLP

(57) ABSTRACT

Metastable liposomal formulations for hydrophobic drug delivery to a tissue or tissue lumen such the bladder have been developed. These are at least one micron in diameter and formed of one or more lipids having entrapped in the lipid a hydrophobic therapeutic, prophylactic or diagnostic agent. The greater stability of these liposomes, as well as the enhanced transfer of entrapped agent into the adjacent tissue, provides for better delivery, especially of hydrophobic agents such as tacrolimus which does not penetrate tissue well. The metastable liposomal formulations can be administered locally, preferably by instillation, or topically, for example, by spraying or painting, to a tissue or tissue lumen such as the bladder in need of treatment.

11 Claims, 3 Drawing Sheets

Low Bounding Efficiency

Medium Bounding Efficiency

Low Degeneracy

High Degeneracy

Low Entropy

High Entropy ( Equilibrium ) Configuration

Related U.S. Application Data

(60) Provisional application No. 61/894,334, filed on Oct. 22, 2013.

(51) Int. Cl.
  *A61K 31/436* (2006.01)
  *A61K 49/00* (2006.01)

(56) References Cited

U.S. PATENT DOCUMENTS

| | | | |
|---|---|---|---|
| 5,043,164 A | 8/1991 | Huang | |
| 5,169,636 A | 12/1992 | Nanba | |
| 5,814,335 A | 9/1998 | Webb | |
| 6,015,576 A | 1/2000 | See | |
| 6,258,378 B1 | 7/2001 | Schneider | |
| 6,354,519 B1 | 3/2002 | Kidooka | |
| 7,049,140 B1 | 5/2006 | Hallahan | |
| 7,063,860 B2 | 6/2006 | Chancellor | |
| 7,491,799 B2 | 2/2009 | Steward | |
| 7,588,172 B2 | 9/2009 | Yamamoto | |
| 7,910,116 B2 | 3/2011 | Aurora | |
| 8,110,217 B2 | 2/2012 | Chancellor | |
| 8,299,040 B2 | 10/2012 | Mehta | |
| 10,639,278 B2 * | 5/2020 | Kaufman | A61K 9/0034 |
| 2002/0058060 A1 | 5/2002 | Kan | |
| 2003/0083299 A1 | 5/2003 | Ferguson | |
| 2003/0124180 A1 | 7/2003 | Ebert | |
| 2003/0143249 A1 | 7/2003 | Lamb | |
| 2004/0018228 A1 | 1/2004 | Fischell | |
| 2004/0028728 A1 | 2/2004 | Fujisaki | |
| 2004/0062797 A1 | 4/2004 | Loeb | |
| 2004/0082521 A1 | 4/2004 | Singh | |
| 2005/0260260 A1 | 11/2005 | Kisak | |
| 2006/0029655 A1 * | 2/2006 | Barenholz | A61K 39/145 424/450 |
| 2006/0115523 A1 * | 6/2006 | Konduri | A61K 9/127 424/450 |
| 2006/0198882 A1 * | 9/2006 | Barenholz | A61K 9/1271 424/450 |
| 2007/0005007 A1 | 1/2007 | Hoogenakker | |
| 2007/0031480 A1 | 2/2007 | Mayer | |
| 2007/0122466 A1 | 5/2007 | Chancellor | |
| 2009/0136443 A1 | 5/2009 | Takeoka | |
| 2009/0214670 A1 | 8/2009 | Mueller | |
| 2011/0250266 A1 * | 10/2011 | Barenholz | A61K 31/445 424/450 |
| 2012/0128762 A1 * | 5/2012 | Chancellor | A61K 9/0034 424/450 |
| 2014/0105989 A1 | 4/2014 | Anderson | |
| 2019/0030187 A1 | 1/2019 | Lu | |

OTHER PUBLICATIONS

Chen, et al., "Determination of the Main Phase Transition Temperature of Phospholipids by Nanoplasmonic Sensing", Scientific Reports, 8(14815):1-11 (2018).
Akar, et al., "Systemic toxicity of tacrolimus given by various routes and the response to dose reduction", Clin. Experiment Ophthalmol., 33(1):53-9 (2005).
Ardhammar, et al., "In vitro membrane penetration of modified peptide nucleic acid (PNA)", J. Biomol. Struct. Dyn., 17:33-40 (1999).
Band, et al., "Recombinant derivatives of botulinum neurotoxin A engineered for trafficking studies and neuronal delivery", Protein Expr. Purif., 71(1):62-73 (2010).
Chang, et al., "Clinically-Proven Liposome-Based Drug Delivery: Formulation, Characterization and Therapeutic Efficacy", Scientific Rep., 1(3):1-8 (2012).
Chuang and Chancellor, "The application of botulinum toxin in the prostate", J. Urol., 176(6 Pt.1):2375-82 (2006).
Chuang, et al., "Intravesical immune suppression by liposomal tacrolimus in cyclophosphamide-induced inflammatory cystit", Neurourol. Urodyn., 30: 421-7 (2011).
Collins, et al., "The stability and structure of cholesterol-rich codispersions of cholesterol and phosphatidylcholine", Journal of Lipid research, 23:291-298 (1982).
Fahr and Seelig, "Liposomal formulations of Cyclosporin A: a biophysical approach to pharmacokinetics and pharmacodynamics", Crit. Rev. Ther. Drug Carrier Syst., 18:141-72 (2001).
Fatouros and Antimisiaris, "Physicochemical properties of liposomes incorporating hydrochlorothiazide and chlorothiazide", J. Drug Target, 9:61-74 (2001).
Gabizon, et al., "Clinical studies of liposome-encapsulated doxorubicin", Acta Oncol., 33: 779-86 (1994).
Grant, et al., Physical biochemistry of a liposomal amphotericin B mixture used for patient treatment, Biochem. Biophys. Acta, 984:11-20 (1989).
Gregoriadis and Ryman, "Liposomes as carriers of enzymes or drugs: a new approach to the treatment of storage diseases", Biochem. J., 124(5):58P (1971).
Gregoriadis, "Liposomes as carriers of drugs. Observations on vesicle fate after injection and its control", Subcell. Biochem., 14: 363-78 (1989).
Gregoriadis, et al., "Improving the therapeutic efficacy of peptides and proteins: a role for polysialic aci", Int. J. Pharm., 300:125-30 (2005).
Gregoridis, et al., "Liposomes in Gaucher type I disease: use in enzyme therapy and the creation of an animal model", Prog. Clin. Biol. Res., 95:681-701 (1982).
Hsueh, et al., "The Effect of Ceramide on Phosphatidylcholine Membranes:A deuterium NMR Study", Biophysical Journal, 82:30089-3095 (2002).
Johnson, et al, "Binding of liposomes to human bladder tumor epithelial cell lines: implications for an intravesical drug delivery system for the treatment of bladder cancer", Selective Cancer Therapeutics, 5(4):148-55 (2009).
Lasic, "Kinetic and Thernodynamic Effects on the Structure and Formation of phosphatidylcholine Vesicles", Hepatology, 13(5):1010-1013 (1991).
Lawrencia, et al., "Transfection of urothelial cells using methyl-beta-cyclodextrin solubilized cholesterol and Dotap", Gene Ther., 8:760-8 (2001).
Lichtenberg, et al., "Liposomes: preparation, characterization, and preservation", Methods Biochem. Anal., 33:337-62 (1988).
Migita and Eguchi, "FK 506-mediated T-cell apoptosis induction", Transplant Proc., 33:2292-3 (2001).
Naesens, et al., "Calcineurin inhibitor nephrotoxicity", Clin. J. Am. Soc. Nephrol., 4:481-508 (2009).
Ng, et al., "Liposomal polyene antibiotics", Methods Enzymol., 391:304-13 (2005).
Nirmal, et al., "Development of potential orphan drug therapy of intravesical liposoma tacrolimas for hemorrhagic cystitis due to increased local drug exposure", J. Urol., 189: 1553-8 (2013).
Nogawa, et al., "Intravesical administration of small interfering RNA targeting PLK-1 successfully prevents the growth of bladder cancer", J. Clin. Invest., 115:978-85 (2005).
Owen, et al., "A phase I clinical evaluation of liposome-entrapped doxorubicin (Lip-Dox) in patients with primary and metastatic hepatic malignancy", Anticancer Drugs, 3:101-7 (1992).
Parkin, et al., "Intravesical dimethyl sulfoxide (DMSO) for interstitial cystitis—a practical appr", Urology., 49:105-7 (1997).
Quinn, "Structure of sphingomyelin bilayers and complexes with cholesterol forming membrane rafts", Langmuir, 29:9447-58 (2013) Abstract Only.
Ranade, "Drug delivery systems—2. Site-specific drug delivery utilizing monoclonal antibodies", J. Clin. Pharmacol., 29:873-84 (1989).
Reimer, et al., "Povidone-Iodine Liposomes;An Overview", Dermatol., 195(Supp 2):93-99(1997).
Rovira-Bru, et al., "Size and Structure of Spontaneously Forming Liposmoes in Lipid/PEG-Lipid Mixtures", Biophyical Journal, 83:2419-2439 (2002).

(56) References Cited

OTHER PUBLICATIONS

Sapra, et al., "Ligand-targeted liposomes for cancer treatment", Curr. Drug Deliv., 2:369-81 (2005).
Senior, "Fate and behavior of liposomes in vivo: a review of controlling factors", Crit. Rev. Ther. Drug Carrier Sys., 3:123-193 (1987).
Smith et al., "Effect of Botulinum Toxin A on the Autonomic Nervous System of the Rat Lower Urinary Tract", J. Urol., 169: 1896-1900 (2003).
Torchilin, "Multifunctional nanocarriers", Adv. Drug Deliv. Rev., 58:1532-55 (2006).
Trevisani, et al., "Ethanol causes inflammation in the airways by a neurogenic and TRPV1-dependent mechanism", J. Pharmacol. Exp. Ther., 309:1167-73 (2004).
Trevisani, et al., "Ethanol elicits and potentiates nociceptor responses via the vanilloid receptor-1", Nat. Neurosci., 5:546-51 (2002).
Tyagi, et al., "Urodynamic and immunohistochemical evaluation of intravesical capsaicin delivery using thermosensitive hydrogel and liposomes", J. Urol., 171:483-9 (2004).
International Search Report and Written Opinion PCT/US2014/061769 dated Jan. 23, 2015.
SDS (siRNA Design Software), http://i.cs.hku.hk/~sirna/software/sirna.php, accessed Aug. 1, 2016.

\* cited by examiner

| Low Bounding Efficiency | Medium Bounding Efficiency | High Bounding Efficiency |
| --- | --- | --- |
| Low Degeneracy | High Degeneracy | Low Degeneracy |
| Low Entropy | High Entropy | Low Entropy |
| | (Equilibrium) Configuration | |

Quantiles

| | | |
|---|---|---|
| 100.0% | maxium | 0.46655 |
| 99.5% | | 0.43588 |
| 97.5% | | 0.39474 |
| 90.0% | | 0.36134 |
| 75.0% | quartilo | 0.32527 |
| 50.0% | median | 0.29465 |
| 25.0% | quartile | 0.26909 |
| 10.0% | | 0.24742 |
| 2.5% | | 0.22327 |
| 0.5% | | 0.20609 |
| 0.0% | minimum | 0.18887 |

Moments

| | |
|---|---|
| Mean | 0.2993883 |
| Std Dov | 0.0439221 |
| Std Err Mean | 0.000437 |
| Upper 95% Mean | 0.3002429 |
| Lower 95% Mean | 0.2985296 |
| N | 10100 |
| Sum Wgt | 10100 |
| Sum | 3023.8011 |
| Variance | 0.0019292 |
| Skewness | 0.5370337 |
| Kurtosis | 0.2434747 |
| CV | 14.670718 |
| N Missing | 0 |

DELIVERY OF AGENTS USING METASTABLE LIPOSOMES

CROSS REFERENCE TO RELATED APPLICATIONS

This application is a continuation of U.S. Ser. No. 15/030,140, filed Apr. 18, 2016, which is a National Phase application under 35 U.S.C. § 371 of International Application No. PCT/2014/061769, entitled "DELIVERY OF AGENTS USING MATASTABLE LIPOSOMES", by Jonathan H. Kaufman and Michael B. Chancellor, filed Oct. 22, 2014, which claims the benefit of and priority to U.S. Ser. No. 61/894,334, filed Oct. 22, 2013, all of which are herein incorporated by reference in their entirety.

FIELD OF THE INVENTION

The invention is generally in the field of metastable liposome for formulations of agents for the treatment of conditions such as of the bladder, especially hemorrhagic cystitis, cancer, and interstitial cystitis/painful bladder syndrome.

BACKGROUND OF THE INVENTION

Millions of people worldwide are afflicted with conditions of the bladder including hemorrhagic cystitis, interstitial cystitis/painful bladder syndrome (IC/PBS), and cancer. Hemorrhagic cystitis is characterized by recurrent hematuria, urinary urgency, and supra pubic pain. IC/PBS is a chronic and painful inflammatory condition affecting about 700,000 to 1 million people in the U.S. alone, of which, ninety percent are women. Urinary bladder cancer is the fourth most frequently diagnosed cancer in men and the ninth most frequently diagnosed cancer in women. There are approximately 56,000 new cases of bladder cancer diagnosed each year. 12,000 deaths each year are attributed to bladder cancer.

Intravesical therapies have been a mainstay in bladder treatments for many years (Parkin, et al., *Urol.*, 49, 105-107 (1997)). Liposomes are biodegradable, non-toxic, unilamellar or multilamellar vesicles formed from naturally occurring or synthetic phospholipids. Liposomes have an ability to entrap and retain a wide range of therapeutic agents, either in their aqueous (hydrophilic agents) or their lipid (hydrophobic) phases (Senior, *Crit. Rev. Ther. Drug Carrier Sys.*, 3, 123-193 (1987); Lichtenberg, *Methods Biochem. Anal.*, 33, 337-362 (1988); Gregoriadis, *Subcell. Biochem.*, 14, 363-378 (1989); Reimer, et al., *Dermatol.*, 195:93 (1997)). Liposomes have been used in clinical practice for treatment of metabolic disorders (Gregoridis, et al., *Prog. Clin. Biol. Res.*, 95, 681-701 (1982), infectious diseases (Richardson, *J. Clin. Pharmacal.*, 29, 873-884 (1983), systemic fungal infections (Grant, et al., *Biochem. Biophys. Acta*, 984, 11-20 (1989) and to reduce the adverse systemic effects of chemotherapeutic drugs (Owen, et al., *Anticancer Drugs*, 3, 101-107 (1992); Gabizon, et al., *Acta Oncol.*, 33, 779-786 (1994)). U.S. Pat. Nos. 7,063,860 and 8,110,217, both by Chancellor, et al., disclose liposomal delivery of capsaicin or botulinum toxin, respectively, to urothelial cells for treatment of bladder dysfunction. Twelve liposomal-therapeutic agent formulations have been approved by the U.S. Federal Drug Administration and an additional twenty-two were in clinical trials (Chang, et al., *Scientific Rep.*, 1,195 (2012)).

Liposomes containing therapeutic agents are delivered to a target cell primarily by whole-liposome endocytosis or phagocytosis and by direct fusion of a liposome membrane with a target cell membrane. Current liposomal therapies primarily utilize the endocytotic pathway due to the small (sub-micron), thermodynamically stable spherical structure of the constituent liposome particles liposomal particles.

Current liposomal formulations have several disadvantages, particularly delivery of hydrophobic agents, due to the small, stable structure of the liposomes. Small liposomes experience great expansive stress and high membrane bending energies due to their small radii of curvature. This forces the small liposomes to be in an entropically unfavorable, yet thermodynamically stable, spherical conformation. Small liposomes have a limited potential to react with membranes of target cells. Current liposomal therapies rely primarily on endocytosis, as opposed to direct membrane fusion, for delivery, which has implications for delivery of hydrophobic agents.

Hydrophobic compounds are often rapidly (within minutes) depleted from the lipid bilayers of liposomes by exchange mechanisms, leading to their equilibration amongst all other lipidic structures within systemic circulation (lipoproteins, erythrocyte membranes, etc.) (Fatouros and Antimisiaris, *J. Drug Target*, 9, 61-74 (2001); Fahr and Seelig, *Crit. Rev. Ther. Drug Carrier Syst.*, 18, 141-172 (2001); Ardhammar et al., *J. Biomol. Struct. Dyn.*, 17, 33-40 (1999)). Rapid clearing of liposomes is not completely absolved by local delivery of liposomal formulations, as lipidic structures also exist in local environments. Uptake by endocytosis is comparatively slow compared to direct fusion with the target cell membrane. Therefore, current liposomal formulations can lose more hydrophobic agent to the environment while undergoing endocytosis, than if the liposomal formulation utilized a more direct pathway. Thus, there is a need for improved methods of hydrophobic therapeutic agent delivery by liposomal formulations.

It is an objective of the invention to provide metastable liposomes which provide improved delivery of hydrophobic therapeutic agents, for example, by direct application to tissue or a tissue lumen such as the bladder for treatment of hemorrhagic cystitis, IC/PBS, cancer and other disorders.

SUMMARY OF THE INVENTION

Metastable liposomal formulations have been developed. These are advantageous for hydrophobic drug delivery to a tissue or tissue lumen such as the bladder. These are at least one micron in diameter and formed of one or more lipids having entrapped in the lipid a hydrophobic therapeutic, prophylactic or diagnostic agent. The greater stability of these liposomes, as well as the enhanced transfer of entrapped agent into the adjacent tissue, provide for better delivery, especially of hydrophobic agents such as tacrolimus which does not penetrate tissue well.

The metastable liposomal formulations can be administered locally, preferably by instillation, or topically, for example, by spraying or painting, to a tissue or tissue lumen such as the bladder in need of treatment.

DETAILED DESCRIPTION OF THE INVENTION

I. Definitions

Figure 1A:
FIGS. 1A, 1B and 1C show conformational microstates of a liposome and an associated bounding efficiency probability and degeneracy.

"Active agent" as used herein refers to a physiologically or pharmacologically active substance that acts locally and/or systemically in the body. An active agent is a substance that is administered to a patient for the treatment (e.g., therapeutic agent), prevention (e.g., prophylactic agent), or diagnosis (e.g., diagnostic agent) of a disease or disorder.

"Hydrophobic" as used herein refers to a non-polar molecule or part of a molecule that cannot form energetically favorable interactions with water molecules and therefore does not dissolve in water.

"Hydrophilic" as used herein describes a polar molecule or part of a molecule that forms enough energetically favorable interactions with water molecules to dissolve readily in water.

"Amphiphilic" as used herein describes a molecule having both hydrophobic and hydrophilic regions, as in a phospholipid or a detergent molecule.

"Effective amount" or "suitable amount" as used herein is at least the minimum concentration required to effect a measurable improvement or prevention of any symptom or a particular condition or disorder, to effect a measurable enhancement of life expectancy, or to generally improve patient quality of life. The effective amount is thus dependent upon the specific biologically active molecule and the specific condition or disorder to be treated. Effective amounts of many proteins, such as monoclonal antibodies (mAbs), are well known in the art. The effective amounts of proteins hereinafter discovered or for treating specific disorders with known proteins, such as mAbs, to be clinically applied to treat additional disorders may be determined by standard techniques which are well within the craft of a skilled artisan, such as a physician.

"Pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

"Fixed shell macrostructure" as used herein refers to the requirement that the arrangement of multiple shell layers maintains a constant topology.

"Continuous" as used herein with reference to the degeneracy function refers to a mathematical function where there are no gaps among coordinates classified as inside a void. In this sense, continuous is synonymous with non-discretized.

"Solvent" as used herein refers to a liquid substance capable of dissolving other substances.

"Object" as used herein refers to a tangible entity (that could include a portion of a solvent), or a portion of space that a tangible entity could occupy.

"Shell" as used herein refers to a deformable boundary of a three-dimensional object that maintains a constant surface area, but not necessarily a constant void volume, during deformation.

"Void" as used herein refers to the three-dimensional space within a shell.

"Volume" as used herein refers to the amount of three-dimensional space an object occupies.

"Void volume" as used herein refers to the volume of a void that is associated with a shell.

"Bounding efficiency of a shell" as used herein refers to the void volume of a shell divided by the volume of a sphere having the same surface area as that of the shell.

"Conformation of a shell" as used herein refers to the shape of a shell.

"Distinguishable conformations of a shell" as used herein refers to conformations of a shell that are not identical.

"Conformational degeneracy of a shell" as used herein refers to the number of distinguishable conformations that a shell could have if the shell were to be deformed in such a way that both the surface area of the shell and the bounding efficiency of the shell are not changed.

"Most entropically favorable bounding efficiency of a shell" as used herein refers to the bounding efficiency of a shell that has the highest conformational degeneracy.

"Phospholipid shell" as used herein refers to a collection of phospholipids in the form of a shell that results from the interaction of phospholipids and an aqueous (or polar) solvent.

"Liposome" as used herein refers to a particle that is composed of one or more connected and/or concentric phospholipid shells.

"Planar projection of a liposome" as used herein refers to the linear mapping of all points of a liposome to corresponding points on a two-dimensional plane such that all lines connecting liposome points to their corresponding projection points are parallel to each other and perpendicular to the projection plane.

"Projection diameter of a liposome" as used herein refers to the diameter of a circle of a size such that it has an area equal to the mean of the areas of all of the liposome's possible planar projections.

"Conformational equilibrium of a liposome" as used herein refers to the liposome being in a conformation that is among the set of conformations that corresponds to the most entropically favorable bounding efficiency of the liposome's collection of phospholipid shells.

"Relative diameter of a liposome" as used herein refers to the ratio of a liposome's projection diameter to the projection diameter that the liposome would have if the liposome was in a state of conformational equilibrium.

"Expansive stress associated with membrane bending" as used herein refers to the internal stress within a membrane, caused by membrane bending, that forces a curved membrane toward a conformation having a relatively larger radius of curvature.

"Metastable liposome" as used herein refers to a liposome that a) has a relative diameter different than 1, and b) is large enough such that the expansive stress associated with membrane bending is not strong enough to overcome the liposome's tendency toward conformational equilibrium.

"One unit in a Euclidean Space having Cartesian coordinates" as used herein refers to the coordinate distance that corresponds to the smallest element of discretization in any of the space's principal directions.

"Adjacent coordinates within a Euclidean Space having Cartesian coordinates" as used herein refers the six coordinates, each along a principle Cartesian axis, with a distance of one unit from the coordinate of concern.

"Natural numbers" as described herein refers to non-negative integers "Countability of a conformational degeneracy" as used herein refers to a condition of a degeneracy such that the conformations within the degeneracy have a one-to-one correspondence with natural numbers.

"Membrane associated agent" as used herein refers to an agent that preferentially partition within or adjacent to a biological membrane versus the membrane's surrounding aqueous solvent.

"Topology of a liposome" as used herein refers to the way in which the liposomes constituent parts are arranged.

II. Metastable Liposomal Formulations

Metastable liposomes having a diameter of at least one micron provide enhanced delivery due to greater stability at the site of delivery. Further enhancement of delivery is achieved by entrapping hydrophobic therapeutic, prophylactic or diagnostic agents within the lipid forming the liposomes. It is believed these liposomes do not necessarily rely upon endocytosis to deliver a hydrophobic active agent to target cells. Instead, the large, metastable liposomes deliver a hydrophobic active agent, such as tacrolimus, by allowing a portion of the liposome containing the hydrophobic active agent to detach and fuse directly with the cell membrane of a target cell, preferably an urothelial cell.

The liposomes may be formulated with one or more excipients. The formulations can be in the form of a liquid or gel, preferably a liquid, for topical application.

A. Metastable Liposomes

Figure 1B:
Figure 1C:
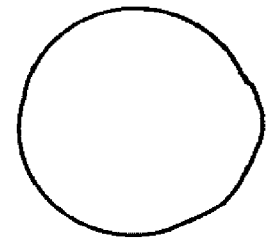

A liposome composed of phospholipid shells that have greater conformational degeneracies has a greater entropy than a liposome composed of the same topology but where its phospholipid shells have a lower conformational degeneracy. As shown in FIG. 1, excluding the existence of external or internal forces, a liposome that has the maximal accessible entropy is at equilibrium. Disregarding the existence of external or internal forces, a liposome is stable when in its equilibrium configuration.

A liposome has is composed of one or more connected and/or concentric phospholipid shells. (Torchilin and Weissig, *Liposomes*, Second Edition, Oxford University Press (2003)). The void volume of a phospholipid shell having a fixed surface area can vary. Thus, a maximum void volume for a shell having a fixed surface area corresponds to the void volume when the shell is in the conformation of a sphere. Likewise, the minimum shell surface area containing a fixed void volume (as in the case of an incompressible fluid bound by the shell) also is associated with the shell being in a conformation of a sphere.

As such, the bounding efficiency of a shell, e, is calculated as $$e = \frac{6\sqrt{\pi V}}{A^{\frac{3}{2}}}$$

where V is the shell void volume and A is the shell surface area.

The bounding efficiency of a shell is positive, unit-less quantity that is normalized such that its maximum equals 1.00. The maximum bounding efficiency corresponds to the bounding efficiency of a spherical shell. Thus, when the void volume is at maximum in a shell of a fixed surface area, the bounding efficiency equals 1.00. The bounding efficiency also equals 1.00 when the shell surface area is at the minimum and the void volume is fixed.

As shown in FIG. 1, the bounding efficiency associated with the maximum conformational degeneracy (and thus maximal entropy), is the equilibrium bounding efficiency, barring influence of any outside potentials (such as membrane bending energies). A phospholipid shell is thermodynamically metastable if the bounding efficiency of the shell is different than the equilibrium bounding efficiency. An increase in bounding efficiency of a phospholipid shell can confer an increase in the relative diameter of the liposome that it is a constituent of. The preferred increase in relative diameter for a liposome to be considered metastable is greater than 1%. The larger the relative diameter becomes, the more reactive the liposome can be. The energy associated with a liposome having a bounding efficiency larger than its equilibrium bounding efficiency is equivalent to the amount of work required to expand the liposome into the entropically disfavored and less degenerate structural conformation.

Liposomes having a projection diameter of less than one micron (small liposomes) cannot achieve a metastable state. These liposomes have high membrane bending energies because of their small radii of curvature, which dominate the entropic effects. Typical small unilamellar liposomes have a spherical conformation with a bounding efficiency of 1.00 and low conformational degeneracy as a direct result of the membrane bending stress. It is impossible for small liposomes to achieve a metastable state because the overriding effects of the membrane bending stresses control the liposome conformation. Therefore, small liposomes are always thermodynamically stable (as opposed to metastable) even though they are not at entropic equilibrium.

In contrast, liposomes having a diameter of greater than one micron have greater radii of curvature and thus experience less expansive stress than small liposomes. As such, large liposomes can be dominated by the entropic forces, as opposed to membrane bending stresses. Therefore, they are able to achieve a metastable state.

The probability distribution of any macroscopic property of an ensemble is equivalent to the degeneracy function of the microstates associated with the macroscopic property of interest (Tolman, *Principles of Statistical Mechanics*, Oxford University Press, (1938)). Here, the macroscopic property of interest is the bounding efficiency probability distribution. Thus, the bounding efficiency probability distribution of a phospholipid shell is equivalent to the degeneracy function of its allowable conformations.

The degeneracy function for an ensemble is related to entropy via the Boltzman equation 5 $k_b$ log g, where S is the conventional thermodynamic entropy, $k_b$ is Boltzmann's constant, and g is the conformational degeneracy. The relationship between energy and entropy, U, for a system of a fixed number of objects, N, is central to the physical definition of temperature, T, $$\frac{1}{T} = \left(\frac{\partial S}{\partial U}\right)_N$$

This definition of temperature is synonymous to the quantity equal for two systems in thermal contact at equilibrium, assuming that such equilibrium occurs when the combined degeneracy of available microstates of the two systems is maximized (Kittel, C. *Thermal Physics*. John Wiley & Sons, Inc. (1969)). When a system is in thermal contact with an infinite reservoir of fixed temperature, as is the case of a non-isolated system at ambient (e.g., room temperature), the combined degeneracy is essentially that of the infinite reservoir. Therefore the resulting probability distribution of energy levels of a system, $\varepsilon_i$, is determined by the partition function, $$P(\varepsilon_l) = \frac{e^{-\varepsilon_l/k_b}}{Z}$$

Where $$Z = \Sigma_l e^{-\varepsilon_l/k_b}$$

and $P(\varepsilon_l)$ is the probability of finding the system in a microstate, l, having the energy, $\varepsilon_l$,
and Z is the partition function.
Thus, the relationship between temperature and average energy for the system is $$U = \langle \varepsilon \rangle = k_b T^2 \frac{\partial}{\partial T} \log Z$$

which is obtained by integrating the energy states weighted by their respective probabilities.

The bounding efficiency associated with the maximum conformational degeneracy (and thus maximal entropy), is the equilibrium bounding efficiency of the system. The energy associated with a system (i.e., a liposome), having a bounding efficiency larger than its equilibrium bounding efficiency is equivalent to the amount of work, W, required to expand the liposome against the pressure, P, associated with the expansive decrease in conformational degeneracy, and a corresponding decrease in entropy. The increase in energy is necessary to move the system away from the entropically favorable equilibrium configuration. The amount of work required is $W=P\Delta V$, where $\Delta V$ is the volume increase and corresponds to a change in bounding efficiency.

The pressure, P, associated with the expansive decrease in conformational degeneracy can be derived analogously to the derivation of the physical definition of temperature using $$\frac{P}{T} = \left(\frac{\partial S}{\partial U}\right)_U.$$

As pressure is a function of volume, $$W = P\Delta V = \int P(V)dV = T\int\int\left(\frac{\partial S}{\partial U}\right)_u dS = T\Delta S$$

which is a familiar thermodynamic identity when dU=0.

An exemplary calculation of a degeneracy function associated with an ensemble of hypothetical phospholipid shells is described in Example 1.

Figure 2:
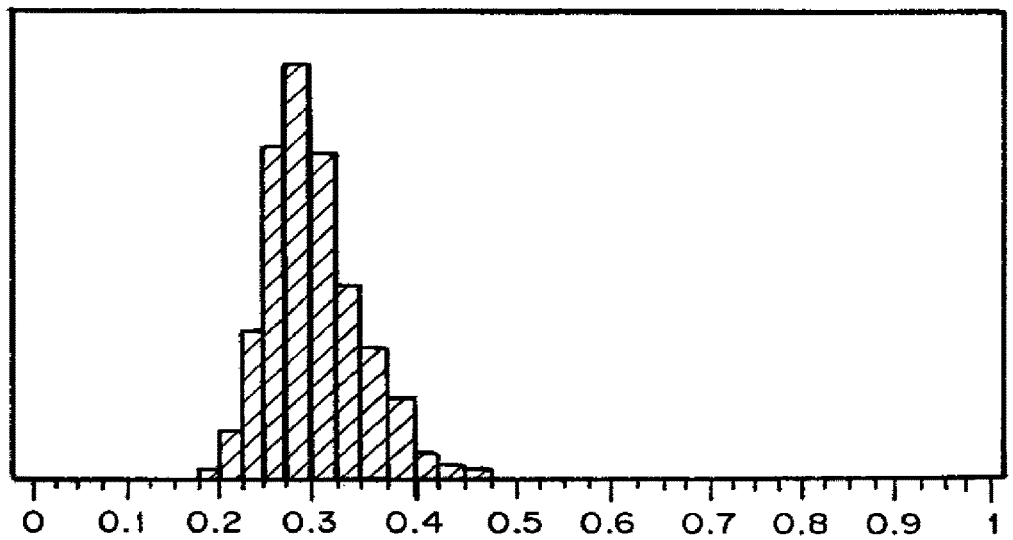
FIG. 2 is an equilibrium bounding efficiency probability distribution of an ensemble of liposomes.

The bounding efficiency probability distribution of a collection of shells is shown in FIG. 2, assuming there are no non-entropic forces affecting the conformation of the liposomes (e.g., membrane bending stresses). In contrast, an ensemble of shells having a bounding efficiency probability distribution that is significantly different from the distribution at equilibrium is not at equilibrium. For example, a collection of shells (that are temporarily impermeable to their void content) having a larger mean bounding efficiency than that of the equilibrium distribution is an example of shells that enclose volumes greater than they would if their membranes were permeable, and thus are consequently metastable as long as the impermeable condition of their constitutive membranes persists. To be considered metastable from a practical sense, the increase in volume can be as little as 1%. A collection of phospholipid shells kept from reaching an equilibrium bounding efficiency distribution by a non-permanent factor, such as an impermeable membrane, is metastable.

Large liposomes have comparatively low membrane bending potentials because of their larger radii of curvature and are consequently controlled by entropic forces. Collections of large liposomes having bounding efficiency probability distributions that significantly deviate from the bounding efficiency probability distribution at equilibrium are metastable.

B. Liposomes

Liposomes are spherical vesicles composed of concentric phospholipid bilayers separated by aqueous compartments. Liposomes can adhere to and form a molecular film on cellular surfaces. Structurally, liposomes are lipid vesicles composed of concentric phospholipid bilayers which enclose an aqueous interior (Gregoriadis, et al., *Int. J. Pharm.*, 300, 125-30 2005; Gregoriadis and Ryman, *Biochem. J.*, 124, 58P (1971)). Hydrophobic compounds associate with the lipid phase, while hydrophilic compounds associate with the aqueous phase.

Liposomes are formed from one or more lipids, which can be neutral, anionic, or cationic at physiologic pH. Suitable neutral and anionic lipids include, but are not limited to, sterols and lipids such as cholesterol, phospholipids, lysolipids, lysophospholipids, sphingolipids or pegylated lipids. Neutral and anionic lipids include, but are not limited to, phosphatidylcholine (PC) (such as egg PC, soy PC), including, but limited to, 1,2-diacyl-glycero-3-phosphocholines; phosphatidylserine (PS), phosphatidylglycerol, phosphatidylinositol (PI); glycolipids; sphingophospholipids such as sphingomyelin and sphingoglycolipids (also known as 1-ceramidyl glucosides) such as ceramide galactopyranoside, gangliosides and cerebrosides; fatty acids, sterols, containing a carboxylic acid group for example, cholesterol; 1,2-diacyl-sn-glycero-3-phosphoethanolamine, including, but not limited to, 1,2-dioleylphosphoethanolamine (DOPE), 1,2-dihexadecylphosphoethanolamine (DHPE), 1,2-distearoylphosphatidylcholine (DSPC), 1,2-dipalmitoyl phosphatidylcholine (DPPC), and 1,2-dimyristoylphosphatidylcholine (DMPC). The lipids can also include various natural (e.g., tissue derived L-α-phosphatidyl: egg yolk, heart, brain, liver, soybean) and/or synthetic (e.g., saturated and unsaturated 1,2-diacyl-sn-glycero-3-phosphocholines, 1-acyl-2-acyl-sn-glycero-3-phosphocholines, 1,2-diheptanoyl-SN-glycero-3-phosphocholine) derivatives of the lipids. In a preferred embodiment, the liposomes contain a phosphaditylcholine (PC) head group, and preferably sphingomyelin. In another embodiment, the liposomes contain DPPC. In a further embodiment, the liposomes contain a neutral lipid, preferably 1,2-dioleoylphosphatidylcholine (DOPC).

In certain embodiments, the liposomes are generated from a single type of phospholipid. In such embodiments, preferably the phospholipid has a phosphaditylcholine head group, and, most preferably is sphingomyelin. The liposomes may include a sphingomyelin metabolite. Sphingomyelin metabolites used to formulate the liposomes include, without limitation, ceramide, sphingosine, or sphingosine 1-phosphate. The concentration of the sphingomyelin metabolites included in the lipids used to formulate the liposomes can range from about 0.1 mol % to about 10 mol %. Preferably from about 2.0 mol % to about 5.0 mol %, and more preferably can be in a concentration of about 1.0 mol %.

Suitable cationic lipids in the liposomes include, but are not limited to, N-[1-(2,3-dioleoyloxy)propyl]-N,N,N-trimethyl ammonium salts, also references as TAP lipids, for example methylsulfate salt. Suitable TAP lipids include, but are not limited to, DOTAP (dioleoyl-), DMTAP (dimyristoyl-), DPTAP (dipalmitoyl-), and DSTAP (distearoyl-). Suitable cationic lipids in the liposomes include, but are not limited to, dimethyldioctadecyl ammonium bromide (DDAB), 1,2-diacyloxy-3-trimethylammonium propanes, N-[1-(2,3-dioloyloxy)propyl]-N,N-dimethyl amine (DODAP), 1,2-diacyloxy-3-dimethylammonium propanes, N-[1-(2,3-dioleyloxy)propyl]-N,N,N-trimethylammonium chloride (DOTMA), 1,2-dialkyloxy-3-dimethylammonium propanes, dioctadecylamidoglycylspermine (DOGS), 3-[N—(N',N'-dimethylamino-ethane)carbamoyl]cholesterol (DC-Chol); 2,3-dioleoyloxy-N-(2-(sperminecarboxamido)-ethyl)-N,N-dimethyl-1-propanaminium trifluoro-acetate (DOSPA), β-alanyl cholesterol, cetyl trimethyl ammonium bromide (CTAB), $diC_{14}$-amidine, N-ferf-butyl-N'-tetradecyl-3-tetradecylamino-propionamidine, N-(alpha-trimethylammonioacetyl)didodecyl-D-glutamate chloride (TMAG), ditetradecanoyl-N-(trimethylammonio-acetyl)di-ethanolamine chloride, 1,3-dioleoyloxy-2-(6-carboxy-spermyl)-propylamide (DOSPER), and N, N, N', N'-tetramethyl-, N'-bis(2-hydroxylethyl)-2,3-dioleoyloxy-1,4-butanediammonium iodide. In one embodiment, the cationic lipids can be 1-[2-(acyloxy)ethyl]2-alkyl(alkenyl)-3-(2-hydroxyethyl)-imidazolinium chloride derivatives, for example, 1-[2-(9(Z)-octadecenoyloxy)ethyl]-2-(8(Z)-heptadecenyl-3-(2-hydroxyethyl)imidazolinium chloride (DOTIM), and 1-[2-(hexadecanoyloxy)ethyl]-2-pentadecyl-3-(2-hydroxyethyl)imidazolinium chloride (DPTIM). In one embodiment, the cationic lipids can be 2,3-dialkyloxypropyl quaternary ammonium compound derivatives containing a hydroxyalkyl moiety on the quaternary amine, for example, 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dioleyloxypropyl-3-dimetyl-hydroxypropyl ammonium bromide (DORIE-HP), 1,2-dioleyl-oxy-propyl-3-dimethyl-hydroxybutyl ammonium bromide (DORIE-HB), 1,2-dioleyloxypropyl-3-dimethyl-hydroxypentyl ammonium bromide (DORIE-Hpe), 1,2-dimyristyloxypropyl-3-dimethyl-hydroxylethyl ammonium bromide (DMRIE), 1,2-dipalmityloxypropyl-3-dimethyl-hydroxyethyl ammonium bromide (DPRIE), and 1,2-disteryloxypropyl-3-dimethyl-hydroxyethyl ammonium bromide (DSRIE).

The lipids may be formed from a combination of more than one lipid, for example, a charged lipid may be combined with a lipid that is non-ionic or uncharged at physiological pH. Non-ionic lipids include, but are not limited to, cholesterol and DOPE (1,2-dioleolylglyceryl phosphatidylethanolamine), with cholesterol being most preferred. The molar ratio of a first phospholipid, such as sphingomyelin, to second lipid can range from about 5:1 to about 1:1 or 3:1 to about 1:1, more preferably from about 1.5:1 to about 1:1, and most preferably, the molar ratio is about 1:1.

The liposomes typically have an aqueous core. The aqueous core can contain water or a mixture of water and alcohol. Suitable alcohols include, but are not limited to, methanol, ethanol, propanol, (such as isopropanol), butanol (such as n-butanol, isobutene, sec-butanol, tart-butanol, pentane (such as amyl alcohol, isobutyl carbinol), hexanol (such as 1-hexanol, 2-hexanol, 3-hexanol), heptanol (such as 1-heptanol, 2-heptanol, 3-heptanol and 4-heptanol) or octanol (such as 1-octanol) or a combination thereof.

The liposomes have either one or several aqueous compartments delineated by either one (unilamellar) or several (multilamellar) phospholipid bilayers (Sapra, et al., *Curr. Drug Deliv.*, 2, 369-81 (2005)). Preferably, the liposomes are multilamellar. Multilamellar liposomes have more lipid bilayers for hydrophobic therapeutic agents to associate with. Thus, potentially greater amounts of therapeutic agent are available within the liposome to reach the target cell. Preferably, the liposomal formulations contain large liposomes ranging from 1 to 100% of the liposome population in the formulation. In some embodiments, large liposomes represent greater than approximately 50% of the liposome population in the formulation.

C. Therapeutic, Prophylactic and Diagnostic Agents

Agents that can be delivered via the metastable liposomal formulations include, but are not limited to, therapeutic, nutritional, prophylactic, and diagnostic agents, that can be encapsulated within the liposomes. These may be small molecules, sugars, polysaccharides, nucleotides, oligonucleotides, lipids, lipoproteins, proteins peptides that are hydrophobic.

The active agent to lipid ratio (International units or weight, micrograms or milligrams, of active agent per mg of lipid) can be controlled to regulate the efficacy of the active agent. Suitable active agent to lipid ratios include, but are not limited to, 1:1, 1:0.9, 1:0.8, 1:0.7, 1:0.6, 1:0.5, 1:0.4, 1:0.3, 1:0.2, or 1:0.1 (activity unit or weight of active agent per mg of lipid).

In certain embodiments, the metastable liposomes contain one or more chemotherapeutic agent. Preferably, the chemotherapeutic is a hydrophobic chemotherapeutic agent effective for treating bladder cancer.

The agents may be inhibitory nucleic acids, including, but not limited to, ribozymes, triplex-forming oligonucleotides (TFOs), antisense DNA, siRNA, and microRNA specific for nucleic acids encoding the chemokines. The antisense DNA oligonucleotides typically include at least 18, 19, 20, 21, 22, 23, 24 or 25 nucleotides and are preferably at least 20 nucleotides in length. Inhibitory nucleic acids and methods of producing them are well known in the art. siRNA design software is available, for example, at http://i.cs.hku.hk/~sirna/software/sirna.php. Synthesis of nucleic acids is well known, see, for example, Molecular Cloning: A Laboratory Manual (Sambrook and Russel eds. $3^{rd}$ ed.) Cold Spring Harbor, N.Y. (2001). The term "siRNA" means a small interfering RNA that is a short-length double-stranded RNA that is not toxic. Generally, there is no particular limitation of the length of siRNA as long as it does not show toxicity. "siRNAs" can be, for example, 15 to 49 bp, preferably 15 to 35 bp, and more preferably 21 to 30 bp long. Alternatively, the double-stranded RNA portion of a final transcription product of siRNA to be expressed can be, for example, 15 to 49 bp, preferably 15 to 35 bp, and more preferably 21 to 30 bp long. In a preferred embodiment, the siRNA is at least 19, 20, 21, 22, or 23 nucleotides long. The double-stranded RNA portions of siRNAs in which two RNA strands pair up are not limited to the completely paired ones, and may contain nonpairing portions due to mismatch (the corresponding nucleotides are not complementary), or bulge (lacking in the corresponding complementary nucleotide on one strand). Non-pairing portions can be contained to the extent that they do not interfere with siRNA formation. The "bulge" preferably comprise 1 to 2 nonpairing nucleotides, and the double-stranded RNA region of siRNAs in which two RNA strands pair up contains preferably 1 to 7, more preferably 1 to 5 bulges. In addition, the "mismatch" used herein is contained in the double-stranded RNA region of siRNAs in which two RNA strands pair up, preferably 1 to 7, more preferably 1 to 5, in number. In a preferable mismatch, one of the nucleotides is guanine, and the other is uracil. Such a mismatch is due to a mutation from C to T, G to A, or mixtures thereof in DNA coding for sense RNA, but not particularly limited to them. Furthermore, the double-stranded RNA region of siRNAs in which two RNA strands pair up may contain both bulge and mismatched, which sum up to, preferably 1 to 7, more preferably 1 to 5 in number.

The terminal structure of siRNA may be either blunt or cohesive (overhanging) as long as siRNA can silence, reduce, or inhibit the target gene expression due to its RNAi effect. The cohesive (overhanging) end structure is not limited only to the 3' overhang, and the 5' overhanging structure may be included as long as it is capable of inducing the RNAi effect. In addition, the number of overhanging nucleotide is not limited to the already reported 2 or 3, but can be any numbers as long as the overhang is capable of inducing the RNAi effect. For example, the overhang consists of 1 to 8, preferably 2 to 4 nucleotides. Herein, the total length of siRNA having cohesive end structure is expressed as the sum of the length of the paired double-stranded portion and that of a pair comprising overhanging single-strands at both ends. For example, in the case of 19 bp double-stranded RNA portion with 4 nucleotide overhangs at both ends, the total length is expressed as 23 bp. Furthermore, since this overhanging sequence has low specificity to a target gene, it is not necessarily complementary (antisense) or identical (sense) to the target gene sequence. Furthermore, as long as siRNA is able to maintain its gene silencing effect on the target gene, siRNA may contain a low molecular weight RNA (which may be a natural RNA molecule such as tRNA, rRNA or viral RNA, or an artificial RNA molecule), for example, in the overhanging portion at its one end. In addition, the terminal structure of the siRNA is not necessarily the cut off structure at both ends as described above, and may have a stem-loop structure in which ends of one side of double-stranded RNA are connected by a linker RNA. The length of the double-stranded RNA region (stem-loop portion) can be, for example, 15 to 49 bp, preferably 15 to 35 bp, and more preferably 21 to 30 bp long. Alternatively, the length of the double-stranded RNA region that is a final transcription product of siRNAs to be expressed is, for example, 15 to 49 bp, preferably 15 to 35 bp, and more preferably 21 to 30 bp long. Furthermore, there is no particular limitation in the length of the linker as long as it has a length so as not to hinder the pairing of the stem portion. miRNAs are produced by the cleavage of short stem-loop precursors by Dicer-like enzymes; whereas, siRNAs are produced by the cleavage of long double-stranded RNA molecules. miRNAs are single-stranded, whereas siRNAs are double-stranded. Methods for producing miRNA are known in the art. Because the sequences for CCL2 (MCP-1), CCL4 (MIP-1β), CCL11 (eotaxin), CXCL1 (GRO-α), sCD40L, IL-2p70/p40, IL-5, sIL-2Rα, IL-6, IL-10, IL-8, and EGF are known, one of skill in the art could readily produce miRNAs that downregulate expression of these chemokines using information that is publicly available.

Increasing the biological activity of growth factors relevant to urological disorders is effective to treat certain urological disorders, in particular interstitial cystitis/painful bladder syndrome and overactive bladder syndrome. The presence of elevated levels of EGF in urine of patients with overactive bladder syndrome is suggestive of tissue repair and fibrosis. An effective amount of one or more growth factors to diminish the severity or number of symptoms of a urological disorder is administered to a subject having one or more symptoms of a urological disorder. Preferred growth factors include, but are not limited to, vascular endothelial growth factor (VEGF), bone morphogenetic protein (BMP), a transforming growth factor (TGF) such as transforming growth factor □, a platelet derived growth factor (PDGF), an epidermal growth factor (EGF), a nerve growth factor (NGF), an insulin-like growth factor (e.g., insulin-like growth factor I), scatter factor/hepatocyte growth factor (HGF), granulocyte/macrophage colony stimulating factor (GMCSF), a glial growth factor (GGF), and a fibroblast growth factor (FGF). The most preferred growth factors is EGF.

In a preferred embodiment for treatment of bladder disease such as overactive bladder, the metastable liposomes can be used to administer a toxin such as a botulinum toxin. Botulinum neurotoxin (BoNT) refers to botulinum serotypes A, B, C, D, E, F, G and all modified, substituted or fragment versions of these toxins that have a blocking effect on snare proteins. These include any substitution or modification of at least 1 amino acid of a naturally produced toxin or synthetically produced toxins. These modifications can be made with recombinant techniques. Also included are toxins with removal or substitution of the binding domain and/or translocation domain. Some of these variations of BoNT types A to G are discussed in U.S. Pat. No. 7,491,799 and by Bland et al. (*Protein Expr. Purif*, 71(1):62-73 (2010)).

Botulinum toxin is produced by *Clostridium botulinum* and is regarded as the most potent biological toxin known (Smith & Chancellor, *J. Urol.*, 171: 2128 (2004)). BoNT has been used effectively to treat different conditions with muscular hypercontraction. BoNT-A is the most common clinically used botulinum toxin among seven immunologically distinct neurotoxins (types A to G). BoNT-A and BoNT-B have been used successfully for the treatment of spinal cord injured patients with neurogenic bladder hyperactivity using intradetrusor BoNT-A injection at multiple sites.

BoNT is known to exert effects by inhibiting acetylcholine ("ACh") release at the neuromuscular junction as well as autonomic neurotransmission. After intramuscular injection of BoNT, temporary chemodenervation and muscle relaxation can be achieved in skeletal muscle as well as in smooth muscle (Chuang & Chancellor, *J. Urol.*, 176 (6 Pt 1):2375-82 (2006)). Smith et al. (*J. Urol.*, 169: 1896 (2003)) found that BoNT injection into the rat proximal urethral sphincter caused marked decreases in labeled norepinephrine at high but not at low electrical field stimulation, indicating that BoNT inhibits norepinephrine release at autonomic nerve terminals.

In one embodiment, the BoNT can be BoNT A-G, preferably BoNT A, C or E, more preferably BoNT A.

The formulations or liposomes optionally contain one or more drugs in place of or in addition to BoNT. These may include antiinfectives such as drugs to treat infections caused by bacteria, fungus, or viruses, analgesics, anti-inflammatories, anti-ulcer medications, antispasmodics, or other drugs used to treat gastric conditions.

The BoNT to lipid ratio (unit of BoNT per mg of lipid) can be controlled to regulate the efficiency of the BoNT. Suitable BoNT to lipid ratios include, but are not limited to, 1:1, 1:0.9, 1:0.8, 1:0.7, 1:0.6, 1:0.5, 1:0.4, 1:0.3, 1:0.2 or 1:0.1 (unit of BoNT per mg of lipid). In one embodiment, the BoNT to lipid ratio is 1:0.5.

Exemplary diagnostic agents include paramagnetic molecules, fluorescent compounds, magnetic molecules, radionuclides, and x-ray imaging agents, and MRI contrast agents.

Preferred representative compounds include anti-inflammatories, angiogenesis inhibitors, and chemotherapeutic agents such as tacrolimus.

Tacrolimus (FK-506 or fujimycin) is a potent immunosuppressive drug. It acts on the innate immune system, specifically the T-cells, by inhibiting calcineurin and resulting in a decrease in both T-lymphocyte signal transduction and interlukin-2 transcription (Migita and Eguchi, *Transplant Proc.*, 33, 2292 (2001)). Despite being a potent immunomodulator, systemic administration of Tacrolimus is limited due to the high incidence of severe adverse effects, including nephrotoxicity and hypertension (Naesens, et al., *Clin. J. Am. Soc. Nephrol.*, 4, 481 (2009); Akar, et al, *Clin. Experiment Ophthalmol.*, 33, 53 (2005)). Traditionally, delivery of tacrolimus, a hydrophobic molecule, to the bladder has been hindered due to its poor aqueous solubility. Recent studies suggest that local liposomal delivery of tacrolimus can overcome issues related to hydrophobicity, while reducing the adverse systemic effects (Chuang, et al., *Neurourolo. Urodynam.*, 30, 421-427 (2011); Nirmal, et al., *J. Urol.*, 189, 1553-1558 (2013)).

In certain embodiments, only one active agent is incorporated into the metastable liposome particles. Preferably, the active agent is hydrophobic, as demonstrated in the Examples. In other embodiments, two or more active agents are incorporated within the metastable liposomal particles.

D. Carriers and Excipients

The liposomes may be formulated with a pharmaceutically acceptable carrier and/or excipient for administration to tissue or a tissue lumen. Suitable carriers include, but are not limited to, sterile liquids, such as water, saline and phosphate buffered saline, and aqueous or water soluble gels such as polyvinyl pyrrolidone, alginate, and hyaluronic acid.

The formulations also can contain minor amounts of wetting or emulsifying agents, or pH buffering agents.

Generally, the liposomes are supplied either separately or mixed together in unit dosage form, for example, as a dry lyophilized powder or water-free concentrate in a hermetically sealed container, such as an ampoule or sachet indicating the quantity of active agent. Where the formulation is to be administered by instillation, it can be dispensed with an instillation bottle containing sterile pharmaceutical grade water or saline.

III. Methods of Manufacturing

Methods of manufacturing liposomes are described in the literature cited above and are well known. These methods seek to produce a liposome with adequate chemical and physical stability in order to achieve the clinical benefit (Torchilin, *Adv. Drug Deliv. Rev.*, 58, 1532-55 (2006)). Thus, typical methods of manufacturing liposomes for liposomal therapies do not result in large metastable liposomes that are stable at room temperature.

In a preferred embodiment, dehydrated metastable liposomes are prepared from a homogenous dispersion of a phospholipid, preferably sphingomyelin, in a tert-butyl alcohol (TBA)/water co-solvent system at a ratio of 2:1 mg sphingomyelin to mL TBA/water. The isotropic monophasic solution of liposomes is freeze dried to generate dehydrated liposomal powder in a sterile vial. The freeze drying step leaves empty lipid vesicles or dehydrated liposomes after removing both water and TBA from the vial. On addition of a pharmaceutically acceptable carrier, such as water, physiological saline or PBS, the lyophilized product spontaneously forms a large, metastable liposome dispersion (see Example 3). The ratio of lipid to TBA is an important factor affecting the size and the polydispersity of resulting liposome preparation.

In one embodiment, metastable liposomal tacrolimus is prepared by a dehydration-rehydration method.

IV. Treatment With Large Metastable Formulations

Incorporation of hydrophobic agents into the lipid components of large, metastable liposomes increases availability during instillation. Localized delivery has the advantage of reducing severe adverse effects associated with systemic delivery. One advantage to using large metastable liposomes, as opposed to small thermodynamically stable liposomes, is that large, metastable liposomes are more reactive with the membrane of target cells, thus delivering the active agent via the membrane fusion pathway as opposed to by endocytosis. A further advantage of the large, metastable liposomes described here is that they are stable at room temperature, yet more reactive than current stable liposomal formulations when in contact with a target cell.

The formulations are administered directly to the tissue or instilled into a tissue lumen. Representative tissue lumens include those of the respiratory, gastrointestinal, and urogenital tracts. These include cavities such as the nasal, pulmonary, esophageal, rectal, bladder, vaginal, urethral, and uterine cavities. In one embodiment the liposomes are formulated into a gel which is applied to the tissue. In another embodiment, the liposomes are suspended in a liquid and spray or painted onto a tissue or instilled into a lumen for an effective amount of time, typically 30 to 60 minutes. The formulations can also be delivered by cystoscopy and an applicator suitable to administer the formulation, including, but not limited to, a spraying device, gauze, roller or sponge. The formulations can be administered by spraying, painting, rolling or sponging, preferably by spraying using a spraying device.

The liposomal encapsulated active agent is preferably administered by instillation into the bladder. Methods of instillation are known. (Lawrencia, et al., *Gene Ther.*, 8:760-8 (2001); Nogawa, et al., *J. Clin. Invest.*, 115:978-85 (2005); Ng, et al., *Methods Enzymol.*, 391:304-13 (2005); Tyagi, et al., *J. Urol.*, 171:483-9 (2004). (Trevisani, et al., *J. Pharmacol. Exp. Ther.*, 309:1167-73 (2004); Trevisani, et al., *Nat. Neurosci.*, 5:546-51 (2002)).

The selected dosage depends upon the desired therapeutic effect, on the route of administration, and on the duration of the treatment desired. Generally dosage levels of 0.001 to 10 mg/kg of body weight daily are administered to mammals. Generally, for intravenous injection or infusion, dosage may be lower.

Certain compositions may also be administered orally, by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration and can be formulated in dosage forms appropriate for each route of administration.

The formulations containing the metastable liposomal active agent can be administered to a desired location in the bladder, other body cavity, or skin by spraying, rolling, painting or sponging a liquid, viscous liquid or gel-like material using a cystoscopy, endoscope, or other suitable scope device. The use of a scope device allows identification of the area of administration before administering the formulation. The scope device can include an applicator for the formulation including, but not limited to, a spraying device, gauze, roller or sponge containing the formulation. The applicator can be protected using a suitable cover until the formulation is to be administered so the formulation is not accidentally applied to an undesired area. The applicator can be attached at the end of the scope device to allow high precision administration. Liquid spray tools for scope devices are known in the art, for example such tool is described in U.S. Pat. Nos. 7,588,172 and 6,354,519 to Yamamoto and Kidooka.

The formulations containing the metastable liposomal hydrophobic active agent can be sprayed in a suitable amount and concentration to a site in the bladder, other body cavity, or skin in need of treatment. The formulations containing metastable liposomal hydrophobic active agent can be painted on the surface of the site to coat the surface with the formulation. For administration techniques involving painting, preferably the formulation is a viscous formulation or gel-like formulation.

One advantage with metastable liposomal tacrolimus or other hydrophobic active agent delivery is the ability to decrease dosage compared to the dosage required when administering a formulation of unencapsulated, or the equivalent stable liposomal formulation, while achieving the same therapeutic effect. The large, metastable liposomes enhance the delivery of the tacrolimus or other hydrophobic active agent, resulting in the effectiveness of lower dosages (see Example 5).

Different size dosage units of the metastable liposomal formulation may be used. A dosage unit containing a dry powder of dehydrated metastable liposomal tacrolimus or other hydrophobic active agent can be reconstituted in a container with a pharmaceutically acceptable carrier. Preferably, the pharmaceutically acceptable carrier is an aqueous carrier. Suitable amounts include, but are not limited to, 0.1-1 mg, 1-3 mg, 3-10 mg, 10-20 mg and 20-50 mg. Suitable concentrations include, but are not limited to, 0.05 mg/ml to 10 mg/ml, preferably 0.05 mg/ml to 5 mg/ml, more preferably 0.05 mg/ml to 2.5 mg/ml.

The relief from a bladder disorder or one or more symptoms thereof can be greater than a week, a few weeks, one, two or three two months, preferably greater than 6 months, following administration of the formulation where the relief does not decline for a prolonged period of time relative to the current therapies. The formulation can be administered with such regularity to provide effective relief from one or more bladder disorder or symptoms associated with bladder disorders.

The metastable liposomal tacrolimus or other active agent is administered to a patient with one or more bladder disorders in a sufficient dose to alleviate the bladder disorder or one or more symptoms of the bladder disorder. Improved efficacy in treatment of bladder disorders is obtained using large metastable liposomal formulations for administration of tacrolimus or other hydrophobic active agents. The liposomes are typically administered in a pharmaceutically acceptable carrier, such as saline or phosphate buffered saline by scintillation into the bladder. Representative bladder disorders that can be treated with the formulations include, but are not limited to, hemorrhagic cystitis, IC/PBS, and cancer. In a preferred embodiment the disorder is hemorrhagic cystitis. These metastable liposomal formulations can also be used to treat disorders of other parts of the body including, but not limited to, the vagina, gastro-intestinal tract (upper and lower), mouth, airway, esophagus, nasal cavity, ear canal, and skin.

Symptoms that can be alleviated by treatment with the metastable liposomal hydrophobic active agent therapies include, but are not limited to, hematuria, urinary urgency, supra pubic pain, inflammation, and urinary retention.

Representative locations for administrations of the metastable liposomal formulations include, but are not limited to, the bladder, vagina, gastro-intestinal tract (upper and lower), mouth, airway, esophagus, nasal cavity, ear canal, and skin. The metastable liposome formulations are particularly well suited for treatment of the epithelial layers of the aforementioned body parts. In the preferred embodiment the location treated with the metastable liposomal formulations is the bladder, particularly the epithelium.

The present invention will be further understood by reference to the following non-limiting examples.

EXAMPLES

Example 1: Determination of the Most Entropically Favorable Bounding Efficiency of a Collection of Phospholipid Shells Consider a collection of liposomes having each member of the collection consist of a single phospholipid shell. The distribution of conformational degeneracy as a function of bounding efficiency can be determined computationally. Both low and high bounding efficiency regions of the function's domain should correspond to relatively low conformational degeneracy, whereas the maximal degeneracy should correspond to some intermediate level of bounding efficiency. See FIG. 1. It is expected that the highest bounding efficiency corresponds to a specific, single structural conformation (a sphere), and thus has a degeneracy of unity. At the other end of the domain, it is expected that the lowest bounding efficiency corresponds to curves "folded" tightly such that they enclose no area. This set of curves should have a lower conformational degeneracy than any set of curves that enclose a finite area. It is expected that the maximum conformational degeneracy occurs at an intermediate value of structural conformational degeneracy.

The degeneracy function can be estimated computationally. This estimation begins with assuming an isotropic three-dimensional Euclidean space described with Cartesian coordinates. In theory, the Euclidean space can be considered continuous, but for computational purposes, the Euclidean space is discretized. The continuous case is an asymptotic limit of increasingly finer degrees of discretization. Each discrete Cartesian coordinate in the Euclidean space can be classified among one of two states: inside the void or outside the void. The volume of a void that is enclosed by a shell is computationally defined as the number of discrete coordinates classified as inside the void. The surface area of the shell that encloses a void is computationally defined as the number of coordinates adjacent to, but not among, the coordinates classified as within the void.

Discretizing the Euclidean space within which the shell (and void) are defined confers countability to the conformational degeneracy. In a continuous case, degeneracy is otherwise difficult to define numerically and thus, not particularly useful. The situation here is analogous to that of a discrete vs. continuous probability distribution when the computational results are interpreted in the context of being an approximation (or representation) of a continuous case.

Given that the definitions of both shell surface area and void volume for the computational estimate of the degeneracy function are both a count of elements of a set of coordinates and are essentially unit-less, it is necessary to provide a distinction between the two regarding dimensionality. The surface area count is multiplied by the square of the unit distance, and the volume count is multiplied by the cube of the unit distance.

The algorithm used to generate the degeneracy function involves the random generation of a large number of three dimensional shapes, where each of the shapes, as formed from discretization, are contiguous, and each of the shapes has the same volume (i.e., the same number of coordinates classified as inside the void). Each shape can be constructed starting with a void having one coordinate at an arbitrary point in the space. The arbitrary point, in each case, is the origin. Next, a shell is generated about the void followed by adding a randomly chosen shell coordinate to the void. The process of adding a randomly chosen shell coordinate to the void is then repeated. The number of repetitions made is dictated by the desired size of the void.

Using this method, it is possible to generate both simply connected voids and voids that are not simply connected. Every void generated by this method will be contiguous. Increasing the size of the volume of voids generated is similar to increasing the fineness of the Cartesian discretization. Therefore, statistical parametric properties of sets of voids may be studied as a function of increasing void size to the extent that such parameters reach an "equilibrium" or asymptotic value. This process can obviate the need to consider the effects of discretization on the results.

Figure 4:
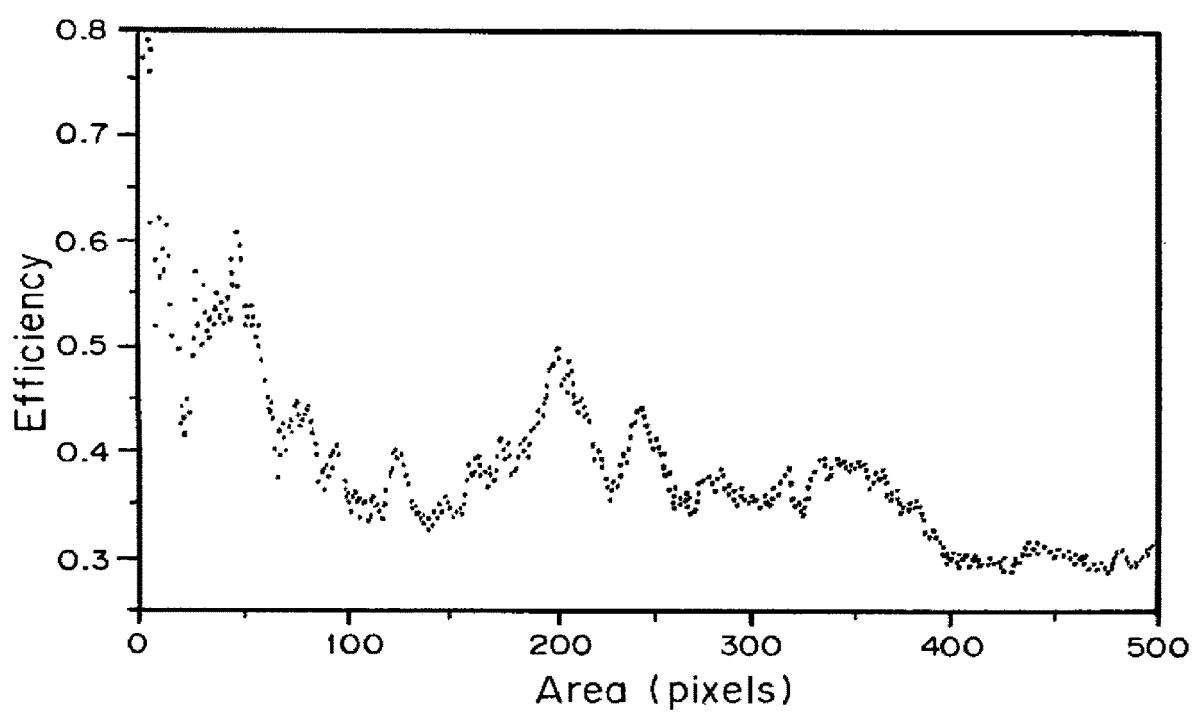
FIG. 4 is a graph comparing bounding efficiency versus void volume of a single growing void.

The parametric property of interest regarding a growing void is the bounding efficiency. FIG. 4 shows the bounding efficiency of a single growing void. The horizontal axis shows void volume in terms of volume as measured by voxels. The vertical axis shows calculated bounding efficiency, which is unit-less. When a sample of 100 randomly generated voids are plotted using the same axes as in FIG. 4 there is significant overlap of the degeneracy functions for voids with volumes less than 20 coordinates. The overlap exists because the possible states of a given void volume in discretized space are quantized into allowable states, and the quantum nature of the model is apparent for small void volumes. Also, this plot indicates that the likely range of bounding efficiencies to be expected for an ensemble of voids is generally independent of void volume. In the sample set of 100 randomly generated voids, the 100 resulting bounding efficiencies is approximately normally distributed with an 80 percent confidence interval of bounding efficiencies ranging between 0.25 and 0.36, with a median value of 0.29. The bounding efficiency distribution of the sample set of 100 randomly generated voids is parametrically described with a mean of 0.300, standard deviation of 0.044, and skewness of 0.537.

Example 2: Determination of the Most Entropically Favorable Bounding Efficiency of a Collection of Liposomes Bounding efficiency of liposomes is difficult to measure directly by experiment. Therefore, to determine the degree to which a liposomal formulation is metastable, the relative diameters of the liposomes contained within the formulation are considered.

Figure 3:
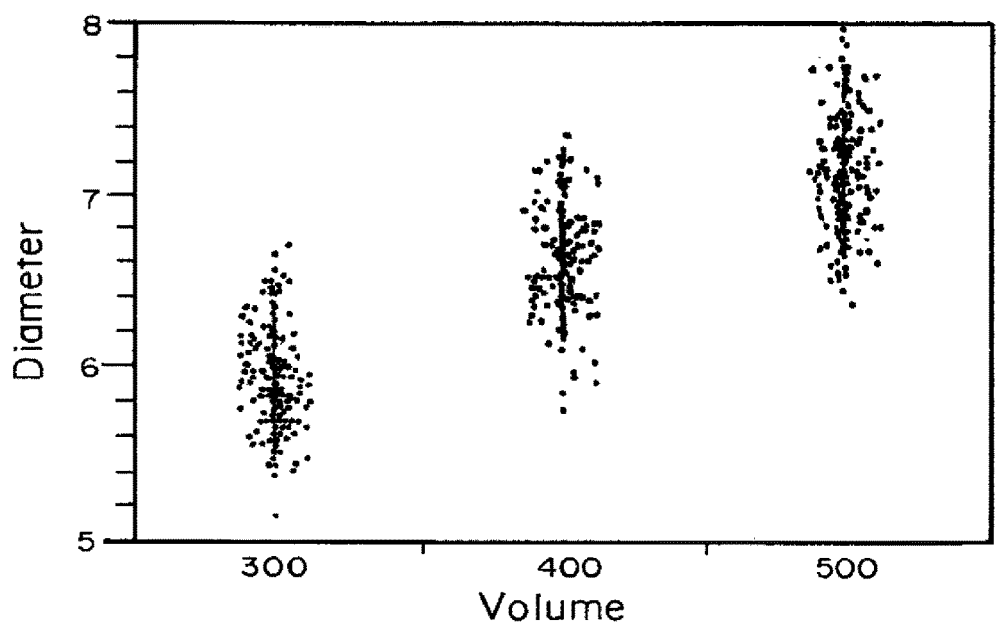
FIG. 3 is a graph of the effect of total metastable liposomal formulation volume on particle diameter.

Regarding the ability to measure relative diameter, it is expected that a resulting measured coefficient of variation of a distribution of liposome projection diameters associated with a collection of liposomes would be artifactually approximately four percent larger than the distribution of the actual liposome projection diameters, as indicated in FIG. 3, which illustrates that the distribution of a large sample set of possible liposome planar projections (the mean of which is the definition of the "projection diameter") has a coefficient of variation of approximately four percent. This difference between measured and actual liposome projection diameter distributions results from the variability that irregularly shaped liposomes may have in terms of their orientation with respect to the direction of observation. Thus, when inferring changes in the distribution of liposome projection diameters associated with changes in inherent bounding efficiencies (or deviations from stable conformations), an expansion of the measured diameter distributions that is purely an artifact of the measurement process must be accounted for.

The degree to which a metastable liposome (or liposome formulation) is out of equilibrium is characterized by its relative diameter. To determine the relative diameter of a metastable liposome, the projection diameter of the metastable liposome is measured both before and after allowing the metastable liposome to reach conformational equilibrium. Then, the ratio (relative diameter) between the before equilibrium and the after equilibrium projection diameters is then evaluated.

A liposome particle in the conformation with the most entropically favorable bounding efficiency has a relative diameter of 1.00. This is the liposome's conformational equilibrium configuration and is its most likely structural conformation, in the absence of other forces acting on or within the liposome. A metastable liposome that has a relative diameter greater than 1.00 would tend to release a portion of its void volume when permitted to reach an equilibrium conformation. This is typically conferred by increasing the permeability of the phospholipid shells of the liposome to the contents of their void volumes.

Example 3: Preparation of Large Metastable Sphingomyelin Liposomes

Methods:

80 mg of pure sphingomyelin (SM) was dissolved in 40 mL of a 2:3 (ratio by volume) of a water to tertiary-butyl alcohol (TBA) mixture. This solution was lyophilized with the following parameters (first freezing at −40° C. for 30 min, then primary drying at 10° C. for 20 h under a vacuum of 200 micron, followed by secondary drying at 20° C. for 4.5 h), and maintained in a vacuum-sealed vial. The lyophilate was then rehydrated with 40 mg of pure water at room temperature (25° C.). Light microscopy of the resulting dispersion of liposomes is shown in FIG. 5. This dispersion was then heated to 55° C., which surpassed the gel-fluid phase transition of the sphingomyelin contents of the liposome's phospholipid shells (Quinn, Langmuir, 29, 9447-9456 (2013)). This phase transition permitted water to diffuse across the liposome's phospholipid shells, resulting in smaller liposomes having entropically favorable bounding efficiencies of their phospholipid shells. The dispersion was the cooled to 25° C.

Results

Upon rehydration, light microscopy revealed metastable sphingomyelin liposomes having a mean diameter of 39.70 microns. The liposomes appear in light microscopy as irregularly shaped particles that are relatively translucent in their center, indicating that there is less membrane (and consequently optical) density in the region interior to each liposome. After heating to 55° C., the mean diameter of the sphingomyelin liposomes decreased to 22.86 microns. Not all liposomes decreased in size, but a sufficient number, approximately 90 percent, of liposomes showed a reduced projection diameter, each affected liposome consequently having a relative diameter of unity. These reduced projection diameter liposomes no longer have a reduced optical density in their interiors. This result is a consequence of an increased amount of phospholipid shell membrane folding in the liposome interior. Based on the calculations described in Example 2, the relative diameter associated with the original metastable distribution is 1.74. Prior to heating, the experimental sphingomyelin liposome dispersion had a relative diameter (1.74) that was shifted away from the equilibrium relative diameter of a thermodynamically stable sphingomyelin liposome dispersion (1.00), and was thus metastable. Water did not diffuse back into the re-suspended sphingomyelin particles upon subsequent cooling to 25° C., as evidenced by a lack of re-inflation to their pre-heating size upon cooling to 25° C., indicating that the temperature-associated reduction of relative diameter was irreversible. Thus, the resulting sphingomyelin dispersion was then at equilibrium, with regard to the relative diameter of the liposomes, and consequently the most entropically favorable bounding efficiency of the liposome's phospholipid shells.

Example 4: Preparation of Large Metastable Sphingomyelin Liposomes that Carry a Near-Infrared (NIR) Dye Methods Eighty mg of pure sphingomyelin and 0.5% (wt/wt) of a membrane-associated NIR fluorescent dye, DIR (1,1'-dioctadecyl-3,3,3',3'-tetramethylindotricarbocyanine iodide) was dissolved in 40 mL of a 2:3 (ratio by volume) water tertiary-butyl alcohol mixture. The resulting solution was lyophilized using the following parameters (first freezing at −40° C. for 30 min, then primary drying at 10° C. for 20 h under vacuum of 200 micron, followed by secondary drying at 20° C. for 4.5 h), and maintained in a vacuum sealed vial. The lyophilate was then rehydrated with 40 mg of pure water at room temperature (25° C.). An aliquot of the re-suspension was heated to 55° C. for five-minutes. The heated aliquot was then cooled to 25° C. The resulting non-heated and heated re-suspensions were diluted 20× and observed using light microscopy to determine conformation of resulting sphingomyelin-NIR dye liposomes.

Results

The sphingomyelin dispersions prepared with a membrane-associated NIR dye showed the same characteristics as the prepared particles of Example 3. The mean diameter of the non-heated, metastable NIR dye-liposomes was 39.7±3.0 microns. The mean diameter of the heated, stable NIR dye-liposomes was 22.9±1.9 microns.

Example 5: Enhanced Near-Infrared (NIR) Dye Delivery Via Metastable Liposomes in Rat Bladder Methods To determine the effectiveness of membrane-associated drug delivery by large metastable particles, after emptying the bladder, 0.5 mL of each (non-heated or heated) dispersion prepared in Example 3 was instilled into the urinary bladder of an anesthetized Sprague-Dawley rat via urethra catheterization and occluding the ureters. The membrane-associated dye combined with the sphingomyelin liposomes was employed as a surrogate marker for any membrane-associated therapeutic agent. The suspensions were incubated in the bladders for 60 minutes. Following incubation, the bladders were harvested, opened, and rinsed in physiological saline. The luminal surfaces were imaged using a camera equipped with a NIR long-pass filter and an excitation source outside the filter range. Intraperitoneal tissue was used as a negative control, representing zero dye deposition.

Results

A comparison of image intensity increase, with respect to the negative control, of the luminal surfaces of the bladders showed that the bladder exposed to the metastable (non-heated) liposomal formulation was significantly brighter than that of the stable (heated) liposomal formulation. Thus, the metastable liposomal formulation delivered more membrane-associated dye to the urothelia than a stable liposomal formulation.

Example 6: Preparation of Large Metastable Liposomes for Treatment of Conditions of the Bladder Large, metastable liposomal formulations may be prepared as described in relation to Examples 3 or 4. However, instead of 0.5% (w/w) of a lipophilic NIR dye, a therapeutically appropriate amount (such as 0.5% to 10% w/w') of tacrolimus or other desired membrane-associated therapeutic agent is mixed with the sphingomyelin or other suitable phospholipid. The resulting metastable therapeutic agent is then instilled into a bladder into a patient thereof for an effective amount of time, typically 30-60 minutes.

We claim:

1. A method of making a dosage formulation, comprising the steps of:
   (a) dispersing lipids capable of forming metastable liposomes in a co-solvent system to create an isotropic monophasic solution;
   (b) lyophilizing the isotropic monophasic solution from step (a) to produce a preliposomal lyophilisate; and
   (c) rehydrating the preliposomal lyophilisate of step (b) to produce the metastable liposomes;
   wherein the metastable liposomes comprise lipids and one or more hydrophobic agents, and have a mean diameter of between one and 100 microns, inclusive,
   wherein the ratio of the mean diameter of the metastable liposomes at 25° C. relative to the mean diameter of the metastable liposomes at 25° C. following heating to a temperature that surpasses the gel-fluid phase transition of the one or more lipids forming the liposomes is greater than 1.0, and
   wherein the one or more hydrophobic agents are entrapped within the lipids forming the liposomes.

2. The method of claim 1, wherein the one or more hydrophobic agents are therapeutic, prophylactic or diagnostic agents encapsulated within the metastable liposomes.

3. The method of claim 1, wherein the one or more hydrophobic agents comprise tacrolimus.

4. The method of claim 1, wherein the lipids forming the metastable liposomes comprise sphingomyelin.

5. The method of claim 1, wherein the co-solvent system comprises water and tert-butyl alcohol.

6. The method of claim 1, wherein in step (c), the preliposomal lyophilisate is rehydrated with a sterile liquid selected from the group consisting of water, saline, phosphate buffered saline, polyvinyl pyrrolidone solution, alginate solution, and hyaluronic acid solution.

7. A method of making a pre-liposomal lyophilisate formulation, comprising:
   (a) dispersing lipids in a co-solvent system to create an isotropic monophasic solution; and (b) lyophilizing the isotropic monophasic solution from step (a) to produce a preliposomal lyophilisate;

wherein the pre-liposomal lyophilisate formulation comprises one or more liposome-forming lipids and one or more hydrophobic agents selected from the group consisting of a therapeutic, prophylactic, and diagnostic agent, wherein the pre-liposomal lyophilisate formulation, after rehydration, is in the form of multilamellar metastable liposomes having a mean diameter of between one and 100 microns, inclusive, wherein the ratio of the mean diameter of the liposomes at 25° C. relative to the mean diameter of the liposomes at 25° C. following heating to a temperature that surpasses the gel-fluid phase transition of one or more of the liposome-forming lipids is greater than 1.0, and wherein the hydrophobic agent is entrapped within the liposome-forming lipids.

8. The method of claim 7, having a ratio of the one or more hydrophobic agents to the liposome-forming lipids at between 1:1 and 1:0.1, inclusive, wherein the ratio is in the form of activity unit or weight of the hydrophobic agent per mg of the liposome-forming lipids.

9. The method of claim 7, wherein the liposome-forming lipids comprise sphingomyelin and the one or more hydrophobic agents comprise tacrolimus.

10. The method of claim 9, comprising 90% sphingomyelin and 10% tacrolimus by weight.

11. The method of claim 7, wherein the co-solvent system comprises water and tert-butyl alcohol.

* * * * *